United States Patent [19]

Myers

[11] 3,993,594

[45] Nov. 23, 1976

[54] ACTIVATING GROUP VIII METAL/ALUMINA CATALYSTS WITH HALOSILANE

[75] Inventor: John W. Myers, Bartlesville, Okla.

[73] Assignee: Phillips Petroleum Company, Bartlesville, Okla.

[22] Filed: Feb. 3, 1975

[21] Appl. No.: 546,819

[52] U.S. Cl. .............................. 252/442; 252/441; 208/112; 260/683.75
[51] Int. Cl.² ..................... B01J 27/08; B01J 27/10
[58] Field of Search ............................ 252/442, 441

[56] References Cited
UNITED STATES PATENTS 3,527,717  9/1970  Giannetti et al. .................. 252/442
3,661,770  5/1972  Givens ............................. 252/441 X

*Primary Examiner*—Patrick P. Garvin

[57] ABSTRACT

A catalyst comprising a Group VIII metal selected from platinum, iridium, osmium, palladium, rhodium, and ruthenium supported on alumina is activated at an elevated temperature with a halosilane such as silicon tetrachloride. In a preferred embodiment, hydrogen is used in conjunction with the halosilane. In another preferred embodiment HCl is used in conjunction with the halosilane. The resulting catalysts exhibit an outstandingly high isomerization rate constant in the isomerization of feedstocks such as normal butane to isobutane.

32 Claims, No Drawings

3,993,594

ACTIVATING GROUP VIII METAL/ALUMINA CATALYSTS WITH HALOSILANE

BACKGROUND OF THE INVENTION

This invention relates to activating catalysts of selected Group VIII metals on alumina.

Platinum supported on alumina has long been used as an isomerization catalyst. It is broadly known to treat such materials with halogens to activate same. However, it has been found that the effectiveness of such treatments can vary widely and are not at all predictable.

SUMMARY OF THE INVENTION

It is an object of this invention to provide a hydrocarbon conversion catalyst of improved activity;

It is a further object of this invention to provide a process for activating a platinum group metal/alumina catalyst utilizing a halosilane;

It is a further object of this invention to provide a platinum group metal/alumina catalyst which is applicable to commercial scale operations; and It is yet a further object of this invention to provide a catalyst capable of effecting isomerization at a higher rate constant.

In accordance with this invention, a catalyst of platinum, iridium, osmium, palladium, rhodium, and ruthenium on alumina is activated in the presence of a halosilane selected from chlorosilanes and bromosilanes at a temperature of greater than 1200° F.

DESCRIPTION OF THE PREFERRED EMBODIMENTS

The catalysts which are activated in accordance with this invention are basically a selected Group VIII metal supported on an active alumina base. The applicable Group VIII metals are at least one of platinum, iridium, osmium, palladium, rhodium, and ruthenium. This class of catalysts is well-known in the prior art and generally contains from 0.01 to 10, preferably 0.1 to 1, weight percent metal based on the total catalyst weight including the alumina base. The preferred metal is platinum. These catalysts can also contain minor amounts of a halogen incorporated during preparation of the catalyst, chlorine and/or fluorine being the two halogens commonly present. Although one or both of these halogens can be present in the catalyst prior to activation by the process of the present invention, the catalyst containing them is not the equivalent of a catalyst which has been activated by the present process. The amount of halogen in the catalyst as prepared (i.e., prior to activation in accordance with this invention) if any, is usually less than about 1.5 weight percent based on the total weight of the catalyst.

To produce these catalysts, an alumina, well-known in the art as an "active" alumina is essential. Active aluminas may be synthetically prepared as by calcination of alumina gels which are formed by adding such reagents as ammonium hydroxide to a salt of aluminum, such as aluminum chloride or aluminum nitrate. These aluminas are generally gamma or eta aluminas depending upon the dehydrating conditions used. Similar active aluminas may be prepared by calcination of naturally occurring aluminas such as the monohydrate and the trihydrate. Bauxite is a common source of active alumina when properly calcined and dehydrated. The alumina base of the catalyst may contain minor amounts of silica and boron oxide. The amounts of these materials should be less than about 30 percent, preferably less than about 10 weight percent of the catalyst base component to produce the most active catalyst.

The halosilane is preferably a chlorosilane, which can be represented by the formula $SiX_4$ in which each X can be the same or different and where at least one X is chlorine and the other X substituents are selected from the group consisting of hydrogen, chlorine and alkyl radicals containing from 1 to 3 carbon atoms per molecule. Exemplary compounds include silicon tetrachloride, trichlorosilane, monochlorosilane, trichloromethylsilane, dichloropropylsilane and the like. A presently preferred compound based on cost and availability is silicon tetrachloride. The corresponding bromosilanes can also be used.

When a hydrogen halide is used in the activating gas along with a halosilane, it is preferred that the halogens in each compound be the same. That is a combination consisting of silicon tetrachloride and hydrogen chloride is preferred rather than silicon tetrachloride and hydrogen bromide, for example.

While it is broadly known to activate platinum/alumina catalysts utilizing a halosilane in the presence of air at a relatively low temperature, it has surprisingly been discovered that activation in the absence of air utilizing a halosilane at a temperature above 1200° F, preferably a temperature within the range of 1250° to 1600° F, more preferably a temperature within the range of 1250° to 1450° F gives a superior catalyst. The air is preferably excluded during the activation of the catalyst to minimize crystal growth of the platinum component which otherwise tends to reduce the effectiveness of the catalyst. Indeed, if the catalyst of this invention is cooled from activation temperature down to 200° to 1000° F in the presence of a halosilane, the activity of the catalyst is diminished.

The Pt, Ir, Os, Ru, Rh, or Pd metal on aluminum catalyst is first calcined in a manner known in the art, for instance, by heating to a temperature within the range of 500–900, more preferably 700°–900° F for a time within the range of 1–10, preferably 1–3 hours. Preferably this is carried out in the presence of air although air is not essential.

The catalyst is then heated to the activation temperature in accordance with this invention of greater than 1200° F, preferably 1250°–1600° F, more preferably 1250°–1450° F. This can be done in either a pure nitrogen atmosphere, a pure hydrogen atmosphere, or in a mixture of nitrogen and hydrogen. Hydrogen is preferred in the sense that excellent results can be obtained in a pure hydrogen atmosphere; however the initial heating from ambient temperature to activation temperature can be carried out in a mixture of hydrogen and nitrogen with essentially the same results as in pure hydrogen and with a cost saving in view of the fact that nitrogen is less expensive. Anhydrous HCl could also be present but it is not required.

The catalyst is then held at this temperature of greater than 1200° F, preferably 1250°–1600° F, more preferably 1250°–1450° F for a time of at least 10 minutes preferably at least one hour. A range of 1.0 to 15 hours, more preferably 1.5 to 5 hours is satisfactory. It is highly preferred during this holding at activation temperature that the atmosphere be hydrogen.

The catalyst is then treated with a dry activating gas comprising the halosilane while at said temperature of greater than 1200° F, preferably 1250°–1600° F, more preferably 1250°–1450° F for a time within the range of 1/10 to 10, preferably 1 to 3 hours. The atmosphere in the reaction chamber is preferably hydrogen. A mixture of hydrogen and anhydrous hydrogen chloride is also quite satisfactory. This is preferably done in the absence of nitrogen, preferably in the absence of both oxygen and nitrogen (i.e., in the absence of air) since both oxygen and nitrogen have a deleterious effect on the catalyst at this point. One convenient method of contacting the catalyst with the halosilane is to utilize a stream of hydrogen carrier gas which stream is divided and 2–20, preferably 5–15 volume percent of the hydrogen is passed through a saturator (a means for bubbling the hydrogen through liquid halosilane) so as to pick up some of the halosilane. Alternatively the halosilane can simply be metered into the hydrogen stream or directly into the zone containing the catalyst. The amount of halosilane in the hydrogen carrier gas will generally be within the range of 0.1 to 20, preferably 1 to 2 mole percent although this can vary greatly depending on the flow rate, the essential feature being the total amount of halosilane introduced. The streams are then combined and the combined stream passed over the catalyst.

The halosilane is contacted with the catalyst in an amount effective to impart a halide content to the catalyst and to increase the activity of the catalyst. In most instances some halide is already present. Generally the halide so added will range from 0.5 to 20, preferably 1 to 12, more preferably 5 to 8 weight percent calculated as the halide ion based on the weight of the catalyst. This is the amount brought into contact with the catalyst with about 80 percent thereof being actually incorporated into the catalyst until the catalyst approaches saturation. The amount of halogen calculated as halide ion actually incorporated by this treatment will generally be within the range of 1–10, preferably 2–6 weight percent halide ion based on the weight of the Pt, Ir, Os, Ru, Rh or Pd metal-alumina. If a saturator is used, the halosilane can be kept in a refrigerated condition either using a wet ice bath or a dry ice bath so as to maintain same in a liquid state where the halosilane has a boiling point below atmospheric temperature at the pressure used.

The thus activated catalyst is then cooled to ambient temperature. Preferably, this cooling is in a hydrogen or hydrogen-nitrogen atmosphere. In a more preferred embodiment, the catalyst is cooled from the above-noted activation temperature to a temperature of about 1100° F or below in pure hydrogen and thereafter cooled on to ambient temperature in an atmosphere containing both hydrogen and nitrogen. It is preferred that the hydrogen during the cooling from the activation temperature to the temperature of approximately 1100° F be passed over the catalyst at a relatively low rate, preferably not more than 0.15 to 0.45 liters per hour for each gram of catalyst until the catalyst is cooled to said temperature of about 1100° F. Thereafter the hydrogen or hydrogen-nitrogen mixture can be passed over the catalyst at a higher rate, but still a rate generally not more than 1.1 to 3.0 liters per hour per gram of catalyst. It is to be noted that during the first portion of the cooling cycle the hydrogen is flowed through the catalyst mass and thus effectively purges most or all of the remaining halosilane. When a mixture of nitrogen and hydrogen are utilized during the heatup or during the cooling after the temperature has been reduced to 900°–1200° F, preferably 900° to 1100° F, the amount of nitrogen can vary from 1 to 99, preferably 5 to 97 mole percent based on the total moles of nitrogen and hydrogen. The procedure should be controlled so that the nitrogen content of the activated catalyst is below 200 parts per million, preferably below 50 parts per million.

Nitrogen can be tolerated without decreased catalyst activity during the entire cooling cycle of anhydrous hydrogen chloride is present. Thus, a cooling gas can comprise anhydrous hydrogen chloride, hydrogen, and nitrogen with nitrogen being the predominant constituent. A preferred ratio of hydrogen to HCl is from 0.5:1 to 2:1 with the nitrogen content being between 50 and 95 mole percent.

It is primarily with respect to long cooling periods such as are encountered in commercial scale operation that it is necessary to remove the halosilane prior to cooling below about 1000° F, preferably before 1100° F, more preferably before cooling below 1200° F.

In an alternative embodiment a mass of said catalyst not yet activated and a separate mass of alumina containing no Group VIII platinum metal component are heated to said temperature of greater than 1200°, preferably 1250°–1600°, more preferably 1250°–1450° F and a stream of activating gas comprising halosilane and hydrogen is passed first through said alumina; the effluent stream from the bed of alumina is then passed directly to the mass of catalyst while still at said temperature of greater than 1200°, preferably 1250°–1600°, more preferably 1250°–1450° F. One convenient method of doing this is simply to have a column packed with the catalyst and at the upstream end thereof a mass of alumina separated from the catalyst by means of quartz wool or the like. Relative amounts of alumina to catalyst can vary greatly, but will generally be within the range of 1 to 50 weight percent, preferably 10 to 30 weight percent alumina based on the total weight of alumina and catalyst.

In another alternate embodiment anhydrous hydrogen chloride can be present during the contacting of the catalyst with the halosilane. These two components can be present in over a wide range of portions. As noted hereinabove, the halosilane can be used alone (that is without any other halogen-containing compound) so the lower limit on the amount of anhydrous HCl is zero. The upper limit, however, can be as high as 90 to 99 percent, or stated in another way, the presence of only a small amount of halosilane in conjunction with anhydrous HCl results in production of an exceptionally effective catalyst.

The catalysts of the present invention are particularly applicable to the skeletal isomerization of isomerizable hydrocarbons including acyclic paraffins, and naphthenes. These catalysts are particularly suitable for the isomerization of straight chain or singly-branched paraffins containing four to eight carbon atoms per molecule including n-butane, n-pentane, n-heptane, methylpentane and the like. Some examples of naphthenes which can be isomerized with these catalysts are methylcyclopentane, dimethylcyclopentane, cyclohexane, methylcyclohexane, and the like.

Actually these are equilibrium reactions as follows:
cyclohexane ⇋ methylcyclopentane
methylcyclohexane ⇋ dimethylcyclopentane
pentane ⇋ methylbutane
n-hexane ⇌ methylpentanes ⇌ dimethylbutanes Conditions can be adjusted to give hydrocracking, as for instance to produce butane from n-octane.

The isomerization reaction conditions and recovery procedures can be varied to achieve the desired conversion in a manner known in the art. A presently preferred isomerization reaction is the isomerization of normal butane to isobutane.

Hydrocarbons to be isomerized are contacted with the activated catalysts prepared in accordance with the invention at an isomerization temperature of about 100°–600° F, more preferably 150°–450° F, in the presence of free hydrogen. The hydrogen-hydrocarbon mol ratios normally used during isomerization are within the range of about 0.25 to 10 to insure long catalyst life. Liquid hourly space velocities, i.e., the volume of liquid charge per hour per volume of catalyst, of about 0.1 to 15 are satisfactory and pressures within the range of atmospheric to 1500 psig in the isomerization zone are suitable.

Maintenance of catalyst activity during the isomerization process is aided by the inclusion of 0.001 to about 1 weight percent chloride in the feed in the form of chlorinated hydrocarbon promoters such as carbon tetrachloride, chloroform, ethyl chloride, isopropyl chloride, etc. This is not a substitute for the activation of the catalyst but it aids in maintaining over long process periods the high level of catalyst activity of the invention catalysts.

The isomerization process can be carried out either in a batchwise or continuous basis, preferably the latter. In a continuous process it is to be understood that hydrogen in the effluent product can be separated and recycled and that recycling of isomerization promoters, if employed, can be practiced. These catalysts are also suitable for hydrocracking operations.

EXAMPLE 1

A gamma-alumina in the form of 1/16 inch dimeter extrudate was impregnated with an aqueous solution of chloroplatinic acid and hydrochloric acid sufficient to give a platinum content of 0.37 weight percent and a chloride content of 1.25 weight percent based on the calcined composite. The impregnated sample was dried in air at 240° F and calcined in air at 800° F for 2 hours. Six equal portions by weight were taken from the calcined catalyst and each portion was heated for two hours in a hydrogen atmosphere at the activation temperature to be used followed by activation in a silicon tetrachloride-hydrogen atmosphere at temperatures given in Table 1. After the heating period, each catalyst was removed from the furnace in its quartz tube, cooled in the activating ambient to about 200° F (12–13 minutes) and transferred to a reactor for testing. The isomerization tests were conducted at about 300°–320° F, at a space velocity of 4 parts liquid feed per part catalyst per hour (by volume, LHSV), 500 psig and a 0.5 hydrogen/feed mole ratio. The feed tested was n-butane containing about 200 ppm chloride as carbon tetrachloride. The results are presented in Table 1.

Table 1

Activation of Chlorided Alumina Platinum Catalyst In Silicon Tetrachloride-Hydrogen Atmosphere

| Run No. | a) $SiCl_4$-$H_2$ Temp. ° F | Time, Hrs | b) Wt. % $SiCl_4$ | c) Relative Isomerization Rate Constant at 315° F |
|---|---|---|---|---|
| 1 | 1002 | 2.0 | 7.5 | 0.11 |
| 2 | 1200 | 2.0 | 7.9 | 1.01 |
| 3 | 1253 | 2.0 | 6.8 | 1.32 |
| 4 | 1355 | 1.8 | 6.5 | 1.79 |
| 5 | 1449 | 1.9 | 5.9 | 1.91 |
| 6 | 1548 | 2.0 | 4.7 | 1.91 | a. The $H_2$ rate was 21 liters/hour (STP) during initial heating and 11 liters/hour during activation. Approximately 1 liter of the 11 liters/hour hydrogen gas was passed through $SiCl_4$ to saturate it with the halide.

b. $SiCl_4$ contacted with the catalyst based on calcined weight of the platinum-alumina.

c. Calculated from the test results using the first order reversible reaction kinetic equations presented on pages 62–63 of "Chemical Reaction Engineering", Levenspiel, John Wiley & Sons, 1962, Library of Congress Catalog No. 62-15185.

The results show that the catalysts increase in activity with increasing activation temperature up to about 1450° F at which point the activity appears to be leveling out. Especially active catalysts are obtained at activation temperatures ranging from about 1250° F to about 1450° F.

Because the cooling time was short it was possible to cool in the presence of the activating ambient. In a commercial scale operation where a longer cooling time (generally about 0.5 to 3 hours) would be required, it is highly preferred to purge any halosilane left from the catalyst with hydrogen prior to cooling.

EXAMPLE 2

Several runs were made to determine the effect of the amount of silicon tetrachloride added to the catalyst during the activating period on the isomerization activity of the resulting catalysts. Extruded gamma-alumina prills were impregnated with an aqueous solution of chloroplatinic acid and hydrochloric acid sufficient to impart a platinum content of 0.37 weight percent and a chloride content of 1.25 weight percent based on the calcined catalyst. The impregnated sample was dried and calcined in air as in the manner of Example 1. The calcined material was divided into portions of equal weight. Each portion was transferred to a quartz tube and heated at an elevated temperature in a silicon tetrachloride-hydrogen ambient and cooled following the procedure of Example 1. The feed tested was n-butane containing about 200 ppm chloride as carbon tetrachloride. The isomerization tests were conducted at 315° F, a space velocity (LHSV) of 4,500 psig reaction pressure and a 0.5 hydrogen/feed mole ratio. The results are presented in Table 2.

Table II

Variation In Isomerization Activity Of Catalyst With Amount Of Silicon Tetrachloride

| Run No. | $SiCl_4$-$H_2$ Temp. °F | Time, Hrs | $SiCl_4$[a] Wt. % | Isomerization Results Isobutane in $C_4$ effluent Mole % | Relative[b] Rate Constant |
|---|---|---|---|---|---|
| 7 | 1354 | 2.0 | 3.8 | 57.1 | 1.33 |
| 8 | 1355 | 1.8 | 6.5 | 61.5 | 1.79 | a. Based on calcined catalyst weight.
b. Calculated as in Example 1.

The results show that more active catalysts are obtained when the amount of silicon tetrachloride used in activating the catalysts exceeds about 4 weight percent. Good results were obtained at 6.5 weight percent as the data demonstrate.

EXAMPLE 3

A platinum-alumina composite was prepared as described in Example 1 hereinabove. Portions of this composite were activated. Activation was carried out in a quartz tube in which a 37.0 gram portion of the platinum-alumina was placed in the tube below an 8.3 gram portion of alumina with quartz wool separating the two substances. The platinum-alumina was activated by heating for two hours in hydrogen alone at 1350° F followed by 2 hours in $H_2$-$SiCl_4$ mixture containing 1.3–1.5 mol percent $SiCl_4$. Activated catalyst was cooled to about 200° F in 3 hours. With one portion, $SiCl_4$ was stopped at the end of the 2-hour period at 1350° F. With the second portion the $SiCl_4$ addition was continued until the average catalyst temperature was 994° F. With a third portion, the $SiCl_4$ addition was continued until the average temperature was 582° F. With a fourth portion, the $SiCl_4$ addition was continued until the average temperature was about 200° F.

Representative samples of these activated catalysts were tested for the isomerization of n-butane at 305° F, four LHSV, 500 psig and with 0.5 $H_2$/butane mol ratio. Relative rate constants calculated from the test data show that stopping the $SiCl_4$ addition at the end of the activation period gave much more active catalysts as is shown in Table 3.

Table III

| Run No. | 9 | 10 | 11 | 12 |
|---|---|---|---|---|
| Activation | | | | |
| Temp, °F | 1351 | 1352 | 1356 | 1354 |
| Time, hrs. | 2.0 | 2.0 | 2.0 | 2.0 |
| $H_2$, l/hr. | 11.5 | 11.3 | 11.3 | 11.3 |
| $SiCl_4$, mol % in $H_2$-$SiCl_4$ | 1.5 | 1.3 | 1.4 | 1.4 |
| Cooling | | | | |
| Temp, $SiCl_4$ stopped, °F | 1354 | 994 | 582 | 200 |
| Time from activation temp. to 200° F | 3.0 | 3.0 | 3.0 | 3.0 |
| $H_2$, l/hr | 10.0 | 11.3 | 11.3 | 11.3 |
|  |  | 10.0[a] | 10.0[a] | 10.0[a] |
| Relative Isomerization Rate constant at 305° F | 1.65 | 1.01 | 0.85 | 0.89 |

[a]$H_2$ 11.3 l/hr until $SiCl_4$ stopped, then reduced to 10.0 l/hr.
10.0 l/hr equivalent to 4.3 cu ft/lb. of platinum-alumina.

These results show that when the cooling time is more than about 0.5 hours, the halosilane should not be present after the catalyst is cooled below activation temperature or at least below about 1100° F.

EXAMPLE 4

A platinum-alumina composite was prepared as described in Example 1. Then this platinum-alumina composite was activated. Activation was carried out in a quartz tube in which a 4 foot portion of the platinum-alumina was placed in the tube below a 1 foot portion of alumina with quartz wool separating the two substances. This 4 foot portion was viewed as four sections of 1-foot each for the purpose of this test. The platinum-alumina was then activated as shown in Table IV hereinbelow and the resulting catalyst subjected to analysis. In addition the catalyst was utilized to isomerize n-butane in the same manner as in the above examples. No nitrogen was present in the preheating and cooling gas.

Table IV

Activation of 5 foot bed

| Run No. | 13 | | | |  |
|---|---|---|---|---|---|
| activation tube packed with 1-ft. of alumina[a] above 4-ft of Pt-alumina[a] | | | | | |
| Section of bed | 1 | 2 | 3 | 4 | 5 |
|  | $Al_2O_3$ |  | Pt-$Al_2O_3$ |  |  |
| Weight, g | 69.5 | 69.5 | 69.5 | 69.5 | 69.5 |
| Activation[b] | | | | | |
| Temp, °F | 1342 | 1342 | 1355 | 1351 | 1354 |
| Time, hr. |  |  | 2.0 |  |  |
| $H_2$, l/hr (SCFH/lb Pt-$Al_2O_3$)[c] |  |  | 88(5.1) |  |  |
| $SiCl_4$ in $H_2$-$SiCl_4$, mol per cent |  |  | 1.5 |  |  |
| $SiCl_4$ wt % of Pt-al calculated as in Example I |  |  | 7.5 |  |  |
| Cooling | | | | | |
| 1350 to 1100° F | | | | | |
| $H_2$, l/hr (SCFH/lb. Pt-$Al_2O_3$) |  |  | 77(4.4) |  |  |
| Time, hrs. |  |  | 1.8 |  |  |
| 1100 to 300° F | | | | | |
| $H_2$, l/hr (SCFH/lb. Pt-$Al_2O_3$) |  |  | 380(22) |  |  |
| Time, hrs. |  |  | 2.6 |  |  |
| Activated Catalyst | | | | | |
| Pt, wt. % | — | 0.38 | 0.36 | 0.39 | 0.37 |
| Cl, wt. % | 2.13 | 3.60 | 3.57 | 3.74 | 3.78 |
| Si, wt. % | 4.94 | 0.27 | 0.12 | 0.11 | 0.11 |
| Surface area, m²/g | 143 | 144 | 139 | 141 | 138 |
| Apparent Bulk Density g/cc | — | — | 0.71 |  |  |
| Nitrogen, ppm | — | — | 1.1 | — | — |
| Isomerization Activity[d] | | | | | |
| $iC_4H_{10}$ in $C_4$ effluent, | — | 60.1 | 62.1 | 62.0 | 61.4 |
| Relative rate constant | — | 1.54 | 1.80 | 1.78 | 1.70 |

[a]Extruded alumina.
[b]Catalysts preheated at 1350° F for 2 hrs. in $H_2$ before activation.
[c]Gas rates at 32° F. (60° F. for SCFH)
[d]Isomerization conditions: 305° F, 4 LHSV, 500 psig, and 0.5 $H_2$/butane mole ratio.

These results show that catalysts of high activity can be produced by passing the halosilane activating agent into contact with an alumina bed and thereafter directly passing the effluent therefrom into contact with the catalyst.

EXAMPLE 5

Another platinum-alumina composite was prepared using a procedure involving holding the composite at 1350° F. for over an hour before chloriding, and with no nitrogen being present during activation. The results are shown hereinbeow in Table V.

Table V

| Run | 14 | | |
|---|---|---|---|
| Section of Pt-$Al_2O_3$ Bed[a] | 1 | 2 | 4 |
| Preheating, R.T. to 1350 F. | | | |

Table V-continued

| | | | |
|---|---|---|---|
| Time, hr. | | 2 | |
| Gas Composition, mole % | | | |
| $H_2$ | | 3.5 | |
| $N_2$ | | 96.5 | |
| Total | | 100.0 | |
| Gas Rate, SCFH/lb Pt-$Al_2O_3$[b] | | 10.0 | |
| Period at 1350 F. before Chloriding | | | |
| Time, hr. | | 1.2 | |
| Gas Composition, mole % | | | |
| $H_2$ | | 3.5 | |
| $N_2$ | | 96.5 | |
| Total | | 100.0 | |
| Gas Rate, SCFH/lb Pt-$Al_2O_3$ | | 10.0 | |
| Chloride Activation | | | |
| Temp. F. | 1345 | 1348 | 1364 |
| Time, hr. | | 2.0 | |
| $H_2$, SCFH/lb Pt-$Al_2O_3$ | | 5.3 | |
| $N_2$, SCFH/lb Pt-$Al_2O_3$ | | 0.0 | |
| $SiCl_4$ in gas, mole % | | 1.57 | |
| $SiCl_4$, wt. % of Pt-$Al_2O_3$ | | 7.7 | |
| Cooling | | | |
| 1350 F. to 1100 F. | | | |
| Time, hr. | | 2.0 | |
| Gas Composition, mole % | | | |
| $H_2$ | | 5 | |
| $N_2$ | | 95 | |
| Total | | 100 | |
| Gas Rate, SCFH/lb Pt-$Al_2O_3$ | | 4.8 | |
| 1100 F. to 300 F. | | | |
| Time, hr. | | 2.4 | |
| Gas Composition, mole % | | | |
| $H_2$ | | 5 | |
| $N_2$ | | 95 | |
| Total | | 100 | |
| Gas Rate, SCFH/lb Pt-$Al_2O_3$ | | 23 | |
| Nitrogen in Activated Catalyst, ppm | 211[c] | 272 | d |
| Isomerization Activity[e] | | | |
| $iC_4H_{10}$ in $C_4H_{10}$ Effluent, Mole % | 56.5 | 53.5 | 52 |
| Relative Rate Constant | 1.26 | 1.09 | 1.01 |

[a]Activation tube packed with 1-ft. of extruded alumina about 4-ft. of 0.35 Pt on alumina.
[b]Gas rates at 60 F.
[c]Nitrogen content of alumina section was 4 ppm.
[d]Not shown.
[e]Isomerization conditions: 305 F, 4 LHSV, 500 psig, and 0.5 $H_2$/butane mole ratio.

These data show that when nitrogen was present in all the preheating and cooling the catalyst contained over 200 ppm (wt.) nitrogen and the rate constant was lower.

EXAMPLE 6

In the following run a lower activity alumina was used than in Example 5 and thus all of the rate constants are lower than would have been the case with an identical alumina. This run does show, however, that nitrogen can be used when cooling from about 1100° F. to about 250° F., if it is avoided in cooling from 1350° to 1100° F. The run also shows that nitrogen can be used during the preheating when the catalyst is maintained in a hydrogen atmosphere for about one hour or longer before chloriding. The nitrogen content of the activated catalyst was only 4 ppm (wt.).

Table VI

| Run | | | 15 | | |
|---|---|---|---|---|---|
| Section of Pt-$Al_2O_3$ Bed[a] | 1 | 2 | | 3 | 4 |
| Preheating, R.T. to 1350 F | | | | | |
| Time, hr. | | | 2.0 | | |
| Gas Composition, mole % | | | | | |
| $H_2$ | | | 20 | | |
| $N_2$ | | | 80 | | |
| Total | | | 100 | | |
| Gas Rate, SCFH/lb Pt-$Al_2O_3$[b] | | | 27.0 | | |
| Period at 1350 F before Chloriding | | | | | |
| Time, hr. | | | 1.5 | | |
| Gas Composition, mole % | | | | | |
| $H_2$ | | | 100 | | |
| Gas Rate, SCFH/lb Pt-$Al_2O_3$ | | | 5.4 | | |
| Chloride Activation | | | | | |
| Temp, F | 1360 | 1373 | | 1354 | 1341 |
| Time, hr. | | | 2.0 | | |
| $H_2$, SCFH/lb Pt-$Al_2O_3$ | | | 6.2 | | |
| $SiCl_4$ in $H_2$-$SiCl_4$, mole % | | | 1.49 | | |
| $SiCl_4$, wt % of Pt-$Al_2O_3$ | | | 8.4 | | |
| Cooling | | | | | |
| 1350 F to 1100 F | | | | | |
| Time, hr | | | 2.0 | | |
| Gas Composition, mole % | | | | | |
| $H_2$ | | | 100 | | |
| Gas Rate, SCFH/lb Pt-$Al_2O_3$ | | | 5.4 | | |
| 1100 to 250 F | | | | | |
| Time, hr. | | | 2.6 | | |
| Gas Composition, mole % | | | | | |
| $H_2$ | | | 20 | | |
| $N_2$ | | | 80 | | |
| Total | | | 100 | | |
| Gas Rate, SCFH/lb Pt-$Al_2O_3$ | | | 27.0 | | |
| Activated Catalyst | | | | | |
| Pt, wt % | 0.36 | 0.36 | | 0.36 | 0.37 |
| Cl, wt % | 3.25 | 3.44 | | 3.67 | 3.82 |
| Si, wt % | 0.70 | 0.10 | | 0.09 | 0.10 |
| Surface Area, m²/g | 140 | 134 | | 139 | 142 |
| Apparent Bulk Density, g/cc | 0.62 | 0.62 | | 0.62 | 0.62 |
| Nitrogen in Activated Catalyst, ppm | 4[c] | 4[c] | | 4[c] | 4[c] |
| Isomerization Activity[d] | | | | | |
| $iC_4H_{10}$ in $C_4$ Effluent | 49.3 | 59.7 | | 58.8 | 58.5 |
| Relative Rate Constant | 0.89 | 1.48 | | 1.40 | 1.38 |

[a]Activation tube packed with 1-ft of extruded alumina above 4-ft of 0.35 Pt on alumina.
[b]Gas rates at 60 F.
[c]Nitrogen content on a blend of this and a duplicate run.
[d]Isomerization conditions: 305 F, 4 LHSV, 500 psig, and 0.5 $H_2$/butane mole ratio.

EXAMPLE 7

A gamma-alumina in the form of 1/16 inch diameter extrudate was impregnated with an aqueous solution of chloroplatinic acid and hydrochloric acid sufficient to give a platinum content of 0.37 weight percent and a chloride content of 1.25 weight percent based on the calcined composite. The impregnated sample was dried in air at 240° F. and calcined in air at 800° F. for 2 hours. Equal portions by weight were taken from the calcined catalyst and each portion was heated for 2 hours in a hydrogen atmosphere followed by activation at about 1250° F. in the medium chosen for 2 hours as shown in the Table. After activation each catalyst was removed from the furnace in its quartz tube, cooled in the activating ambient to about 200° F. (12–13 minutes) and transferred to a reactor for testing. The isomerization tests were conducted at about 305°–325° F. at a space velocity of 4 parts liquid feed per part catalyst per hour (by volume, LHSV), 500 psig and a 0.5 hydrogen/feed mole ratio. The feed tested was n-butane containing about 200 ppm chloride as carbon tetrachloride. The results are presented in the Table.

Table VII

| Run | Amount of $SiCl_4$ Added to Activating Gas Wt % of HCl[a] | Isomerization Results at 305–325° F. Isobutanes in $C_4$ Effluent, Mole 9 | Relative rate Constant[b] |
|---|---|---|---|
| 16 | none | 53.3 | 1.09 |
| 17 | 1.2 | 58.0 | 1.40 |
| 18 | 2.8 | 58.0 | 1.40 |

[a]Unpromoted ambient consisted of 62 mole per cent HCl and 38 mole percent $H_2$. The activation gas flow was 29 liters per hour at STP. The $SiCl_4$ was added by passing a portion of the $H_2$ through the silicon tetrachloride.
[b]Calculated from the test results using the first order reversible reaction kinetic equations presented on pages 62-63 of "Chemical Reaction Engineering" Levenspiel, John Wiley & Sons, 1962, Library of Congress Catalog No. 62-15185.

This shows the effect of silicon tetrahalides in combination with HCl, whereby an improved relative rate constant is achieved.

While this invention has been described in detail for the purpose of illustration, it is not to be construed as limited thereby but is intended to cover all changes and modifications within the spirit and scope thereof.

What is claimed is:

1. A method for activating an alumina supported Pt, Ir, Os, Ru, Rh or Pd metal catalyst which comprises:
   heating said catalyst to a temperature of greater than 1200° F in an atmosphere selected from the group consisting of nitrogen, hydrogen, and mixtures of nitrogen and hydrogen;
   holding the thus treated catalyst at said temperature of greater than 1200° F for at least 10 minutes and contacting said catalyst at said temperature of greater than 1200° F with a dry activating gas comprising a halosilane selected from the group consisting of chlorosilanes and bromosilanes for a time sufficient to impart a halide content to the catalyst and to increase the activity of the catalyst, said contacting being carried out in the absence of air; and
   thereafter cooling said thus contacted catalyst.
2. A method according to claim 1 wherein said temperature is within the range of 1250° to 1600° F.
3. A method according to claim 1 wherein said temperature is within the range of 1250° to 1450° F and said halosilane is a chlorosilane of the formula $SiX_4$ in which each X can be the same or different and where at least one X is chlorine and the other X substituents are selected from the group consisting of hydrogen, chlorine and alkyl radicals containing from 1 to 3 carbon atoms per molecule.
4. A method according to claim 3 wherein said chlorosilane is $SiCl_4$ and chlorine as chlorine ion is incorporated in an amount within the range of 1–10 weight percent based on the weight of said catalyst.
5. A method according to claim 1 wherein said halosilane is $SiCl_4$.
6. A method according to claim 1 wherein said halosilane is carried by a stream of hydrogen.
7. A method according to claim 1 wherein said metal is platinum.
8. A method according to claim 1 wherein said thus contacted catalyst is cooled to 1100° F in the absence of nitrogen and in the presence of hydrogen.
9. A method according to claim 8 wherein said alumina supported metal catalyst is held at said temperature of greater than 1200° F in the absence of nitrogen in the presence of hydrogen for a time within the range of 0.1 to 15 hours after said heating and before said contacting.
10. A method according to claim 9 wherein said temperature during said contacting is within the range of 1250° to 1450° F and said halosilane is $SiCl_4$ and said metal is platinum present in an amount within the range of 0.1 to 1 weight percent based on the weight of said catalyst.
11. A method according to claim 1 wherein said thus contacted catalyst is cooled to 1100° F in the absence of nitrogen and in the presence of hydrogen and then to room temperature in the presence of hydrogen and nitrogen.
12. A method according to claim 1 wherein said thus contacted catalyst is flushed substantially free of said halosilane before cooling below 1100° F.
13. A method according to claim 1 wherein there is present in addition HCl during said contacting.
14. A catalyst prepared according to the method of claim 1.
15. A method for activating an alumina suported Pt, Ir, Os, Ru, Rh, or Pd metal catalyst comprising:
   passing a dry activating gas comprising a halosilane through a bed of alumina at a temperature of greater than 1200° F and thereafter passing the effluent from said alumina bed directly into contact with said alumina supported metal catalyst also at a temperature of greater than 1200° F for a time sufficient to impart a halide content to the catalyst and to increase the activity of the catalyst; and
   thereafter cooling said thus contacted catalyst.
16. A method according to claim 15 wherein said temperature of said alumina and of said catalyst is within the range of 1250° to 1600° F and said contacting is carried out in the substantial absence of nitrogen.
17. A method according to claim 15 wherein said temperature of said alumina and of said catalyst is within the range of 1250° to 1450° F, said contacting is carried out in the substantial absence of nitrogen, and said halosilane is a chlorosilane of the formula $SiX_4$ in which each X can be the same or different and wherein at least one X is chlorine and the other X substituents are selected from the group consisting of hydrogen, chlorine and alkyl radicals containing from 1 to 3 carbon atoms per molecule.
18. A method according to claim 15 wherein said temperature of said alumina and of said catalyst is within the range of 1250° to 1450° F and said halosilane is a chlorosilane having the formula SiX$_4$ wherein each X can be the same or different and where at least one X is chlorine and the other X substituents are selected from the group consisting of hydrogen, chlorine and alkyl radicals containing 1 to 3 carbon atoms per molecule.

19. A method according to claim 18 wherein said chlorosilane is SiCl$_4$.

20. A method according to claim 15 wherein said halosilane is SiCl$_4$.

21. A method according to claim 15 wherein said halosilane is carried in a stream of hydrogen, said contacting being carried out in the absence of nitrogen.

22. A method according to claim 15 wherein said metal is platinum and said contacting is carried out in the absence of nitrogen.

23. A method according to claim 15 wherein said thus contacted catalyst is cooled to 1100° F in the absence of nitrogen in the presence of hydrogen.

24. A method according to claim 23 wherein said catalyst is held at a temperature of greater than 1200° F in the presence of hydrogen and the absence of nitrogen before said contact with said halosilane.

25. A method of activating an alumina supported Pt, Ir, Os, Ru, Rh, or Pd metal catalyst comprising heating said catalyst to a temperature of greater than 1200° F in an atmosphere of nitrogen and hydrogen; holding said catalyst at said temperature in a hydrogen atmosphere in the substantial absence of nitrogen for a time of at least 10 minutes; thereafter treating said thus heated catalyst with a dry activating gas comprising a chlorosilane to impart chlorine as chloride ion to said catalyst; cooling said catalyst to a temperature of 1100° F or below in the presence of hydrogen and the absence of nitrogen; and thereafter cooling in the presence of nitrogen and hydrogen.

26. A method according to claim 25 wherein said catalyst is treated with said activating gas to a temperature within the range of 1250° to 1600° F and said cooling of said catalyst in the presence of hydrogen is carried out to a temperature within the range of 900° to 1100° F, and wherein no hydrogen halide is present during said treating.

27. A method according to claim 1 wherein said cooling takes place in the presence of anhydrous hydrogen chloride.

28. A method according to claim 27 wherein said halosilane is SiCl$_4$.

29. A method according to claim 28 wherein said cooling takes place in an atmosphere comprising said anhydrous hydrogen chloride, hydrogen, and 50 to 95 mole percent nitrogen, the ratio of said hydrogen to said anhydrous hydrogen chloride being within the range of 0.5:1 to 2:1.

30. A method according to claim 27 wherein said cooling takes place in an atmosphere comprising said anhydrous hydrogen chloride, hydrogen, and 50 to 95 mole percent nitrogen, the ratio of said hydrogen to said anhydrous hydrogen chloride being within the range of 0.5:1 to 2:1.

31. A method according to claim 1 wherein said contacting takes place in the absence of nitrogen and oxygen.

32. A method according to claim 15 wherein said thus contacted catalyst is cooled to 1100° F. in the absence of nitrogen and in the presence of hydrogen and then is cooled to room temperature in the presence of hydrogen and nitrogen.

* * * * *